United States Patent
Wu et al.

(10) Patent No.: US 10,399,981 B2
(45) Date of Patent: Sep. 3, 2019

(54) CRYSTAL FORM A OF 7-(CYCLOPROPYLMETHYL)-1-(((CIS)-4-HYDROXY-4-METHYLCYCLOHEXYL) METHYL)-3-METHYL-1H-PURINE-2,6-(3H, 7H)-DIONE FOR TREATING LIVER DISEASES

(71) Applicant: GUANGDONG RAYNOVENT BIOTECH CO., LTD., Guangdong (CN)

(72) Inventors: Lingyun Wu, Shanghai (CN); Chaofeng Long, Dongguan (CN); Peng Zhang, Shanghai (CN); Xiaoxin Chen, Dongguan (CN); Li Zhang, Shanghai (CN); Zhuowei Liu, Dongguan (CN); Zheng Wang, Shanghai (CN); Shuhui Chen, Shanghai (CN); Lijuan Chen, Dongguan (CN)

(73) Assignee: GUANGDONG RAYNOVENT BIOTECH CO., LTD., Guangdong (CN)

(*) Notice: Subject to any disclaimer, the term of this patent is extended or adjusted under 35 U.S.C. 154(b) by 0 days.

(21) Appl. No.: 15/771,845

(22) PCT Filed: Oct. 27, 2016

(86) PCT No.: PCT/CN2016/103487
§ 371 (c)(1),
(2) Date: Apr. 27, 2018

(87) PCT Pub. No.: WO2017/071607
PCT Pub. Date: May 4, 2017

(65) Prior Publication Data
US 2018/0305361 A1    Oct. 25, 2018

(30) Foreign Application Priority Data
Oct. 29, 2015 (CN) .......................... 2015 1 0719196

(51) Int. Cl.
*A61K 31/522* (2006.01)
*C07D 473/04* (2006.01)

(52) U.S. Cl.
CPC .......... *C07D 473/04* (2013.01); *A61K 31/522* (2013.01); *C07B 2200/13* (2013.01)

(58) Field of Classification Search
CPC ........................... A61K 31/522; C07D 473/04
USPC ....................................... 514/263.34; 544/267
See application file for complete search history.

(56) References Cited

U.S. PATENT DOCUMENTS 5,321,029 A    6/1994 Maschler

FOREIGN PATENT DOCUMENTS

| EP | 3205652 A1 | 8/2017 |
|---|---|---|
| WO | WO 9209203 | 6/1992 |
| WO | WO 9317684 | 9/1993 |
| WO | WO 9852948 | 11/1998 |
| WO | WO 2006104870 | 10/2006 |
| WO | WO 2016054971 | 4/2016 |
| WO | WO 17/071607 | * 5/2017 |

OTHER PUBLICATIONS

Jordan, V. C. Nature Reviews: Drug Discovery, 2, 2003, 205.*
Hackam, et al. JAMA, 296(14), 2006, 1731-1732.*
Extended European Search Report for the corresponding European Patent No. 16859042.0, dated Jul. 24, 2018.

* cited by examiner

*Primary Examiner* — Douglas M Willis
(74) *Attorney, Agent, or Firm* — Leason Ellis LLP

(57) ABSTRACT

The invention discloses a crystal form A of a compound (I) and a preparation method thereof, and further discloses an application of the crystal form A as a PDE2 or TNF-α inhibitor.

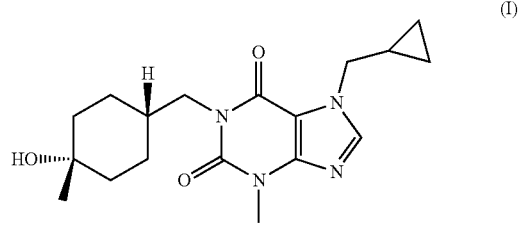

(I)

17 Claims, 2 Drawing Sheets

CRYSTAL FORM A OF 7-(CYCLOPROPYLMETHYL)-1-(((CIS)-4-HYDROXY-4-METHYLCYCLOHEXYL)METHYL)-3-METHYL-1H-PURINE-2,6-(3H,7H)-DIONE FOR TREATING LIVER DISEASES

CROSS-REFERENCE TO RELATED PATENT APPLICATIONS

This application is a U.S. National Phase Application under 35 U.S.C. § 371 of International Patent Application No. PCT/CN2016/103487, filed Oct. 27, 2016, and claims the priority of Chinese Application No. 201510719196.4, filed Oct. 29, 2015, all of which are incorporated by reference in their entireties. The International Application was published on May 4, 2017 as International Publication No. WO 2017/071607 A1.

FIELD OF INVENTION

The invention relates to a crystal form A of a compound (I) and a preparation method thereof, as well as the application of the crystal form A as a PDE2 or TNF-α inhibitor.

PRIOR ARTS

Phosphodiesterase (PDE) catalyzes hydrolysis of cyclic nucleotides cGMP and cAMP, and regulates various physiological responses by controlling intramolecular concentrations of the two important secondary signaling factors. Abnormal intramolecular regulation of cyclic nucleotides cGMP and cAMP is the cause of many diseases. At present, many drugs improve and treat diseases by inhibiting PDE activities. For example, PDE5 inhibitor is used for pulmonary hypertension, and PDE4 inhibitor is used for arthritis caused by psoriasis. At present, a total of 11 major classes of phosphodiesterase genes are known, and each class includes a number of subtypes, which is more than 100 PDE subtypes in total. Different subtypes have different structures and different tissue distributions, and show greatly different activities to cyclic nucleotides cGMP and cAMP, and show greatly different ability of regulate to physiological functions.

PDE2 phosphodiesterase can catalyze hydrolysis of cyclic nucleotides cGMP and cAMP, and the activity of cAMP is regulated by cGMP, so PDE2 plays a key role in balancing the intracellular cGMP and cAMP. PDE2 is widely expressed in human tissues, and is mainly distributed in the heart, central nervous system, liver, adrenal gland, endothelial cells, platelets and the like. PDE2 involves in regulation of various physiological activities, such as the processes of learning, memory and cognition in nervous centralis, maintaining the basic rhythms of the heart, smooth muscle and endothelial cells and maintaining permeability of the endothelial cell, and regulating inflammatory responses. Knockout of PDE2 in mice directly leads to fetal death. The strategy of inhibiting PDE2 activities may be used for treating various central and cardiovascular diseases, and controlling inflammatory responses.

Non-selective PDE inhibition activities shown in a plurality of natural and synthetic purine compounds have been discovered early, such as caffeine, theophylline and pentoxifylline. Pentoxifylline (PDE2 activity) is approved for the treatment of lower limb lameness caused by peripheral vascular blockage, and it mainly plays a role as reducing blood viscosity, improving erythrocyte deformation, inhibiting platelet aggregation, and so on. Novel PDE2 inhibitors with high selectivity have also been reported to be used in controlling endothelial cell division and revascularization, as well as improving central cognitive impairment. However, in general, the development and application of novel selective PDE2 inhibitors are still limited, and the discovery and application of novel PDE2 inhibitors show broad prospects.

Tumor necrosis factor α (TNF-α) is a cytokine with varies of biological activities, and has important influence on the incidence, development and treatment of many diseases, especially diseases related to immune and inflammation. TNF-α is mainly produced by monocytes and macrophages, and is involved in immune regulation and cytokine network coordination of organisms. Under normal circumstances, TNF-α plays an important role in immune defense and immune surveillance, but has adverse effects in some circumstances. Researches show that overexpression of TNF-α may induce the expression of proinflammatory cytokine, such as interleukon-1 (IL-1) and IL-6, increase endothelial cell permeability, increase the expression of adhesion molecules, activate neutrophils and acidophils, and induce synovial cells and cartilage cells to secrete acute phase substances, tissue degradase and the like, which promote inflammation. These pathological responses play a very important role in the incidence and development of many immune-mediated inflammatory diseases (IMID), such as rheumatoid arthritis (RA), psoriatic arthritis (PsA), ankylosing spondylitis (AS), inflammatory bowel disease (IBD), juvenile chronic arthritis (JCA) and vasculitis. Researches show that TNF-α is a desired target of the plurality of IMIDs. Moreover, for some diseases caused by long-time injury or chronic inflammation, such as fatty hepatitis and chronic obstructive pulmonary disease, the use of TNF-α antagonist drugs (TNF-α inhibitors) to neutralizing excessive TNF-α is effective prevention and treatment approaches. The clinical use of TNF-α monoclonal drugs have proved that inhibiting TNF-α is very effective means for treating the inflammation-associated diseases. PDE2 can regulate the expression of TNF-α from the mechanism. Therefore, the TNF-α level can be controlled by regulating PDE2 activities, thereby realizing the control over inflammatory responses.

CONTENT OF THE PRESENT INVENTION

The invention provides a crystal form A of a compound (I), which has an XRPD pattern as shown in FIG. 1,

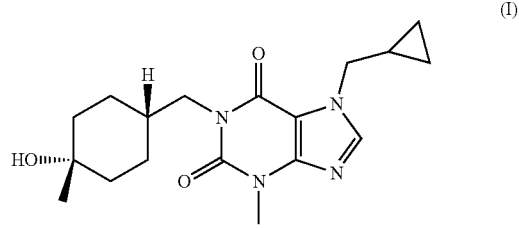 [SMILES: Cn1c(=O)n(C[C@H]2CC[C@@](C)(O)CC2)c(=O)c2c1ncn2CC1CC1]

In some embodiments according to the invention, the data of the XRPD pattern of the crystal form A are shown in Table 1.

TABLE 1

Analysis Data of XRPD Pattern of Crystal Form A

| No. | 2-Theta | I % |
|---|---|---|
| 1 | 9.578 | 100 |
| 2 | 10.43 | 40.1 |
| 3 | 12.502 | 18.2 |
| 4 | 13.996 | 4 |
| 5 | 15.086 | 7.7 |
| 6 | 15.38 | 16.5 |
| 7 | 16.287 | 7.4 |
| 8 | 16.661 | 6.3 |
| 9 | 17.428 | 85.8 |
| 10 | 17.646 | 29.8 |
| 11 | 18.298 | 11.3 |
| 12 | 19.977 | 10.2 |
| 13 | 20.427 | 10.2 |
| 14 | 20.879 | 29.7 |
| 15 | 21.314 | 8.6 |
| 16 | 22.141 | 31.1 |
| 17 | 22.928 | 6.4 |
| 18 | 23.387 | 4.4 |
| 19 | 24.27 | 4.6 |
| 20 | 24.548 | 39.8 |
| 21 | 25.116 | 3 |
| 22 | 25.834 | 9.5 |
| 23 | 26.719 | 5.3 |
| 24 | 27.665 | 3.6 |
| 25 | 29.477 | 16 |
| 26 | 30.956 | 5.6 |
| 27 | 32.416 | 3.4 |
| 28 | 34.623 | 3.4 |
| 29 | 37.243 | 3.5 |
| 30 | 39.237 | 3.6 |

In some embodiments according to the invention, the preparation method of the crystal form A mentioned above includes dissolving any form of the compound (I) in ester solvent, alcoholic solvent, acetonitrile, acetone or mixed solvent of the alcoholic solvent with water while heating, and then cooling crystallization.

In some embodiments according to the invention, the preparation method mentioned above further includes step of concentrating the solvent to 1/30-1/2 of its original volume, after the step of dissolving while heating.

In some embodiments according to the invention, the preparation method mentioned above further includes step of concentrating the solvent to 1/20-1/5 of its original volume, after the step of dissolving while heating.

In some embodiments according to the invention, the weight ratio of the compound (I) to the solvent is selected from 10:1 to 1:1.

In some embodiments according to the invention, the weight ratio of the compound (I) to the solvent is selected from 6:1 to 3:1.

In some embodiments according to the invention, the weight ratio of the compound (I) to the solvent is selected from 5:1 to 4:1.

In some embodiments according to the invention, the mentioned heating temperature is selected from 40° C. to refluxing temperature.

In some embodiments according to the invention, the mentioned heating temperature is selected from 50° C. to 60° C.

In some embodiments according to the invention, the mentioned cooling crystallization temperature is selected from 0° C. to 30° C.

In some embodiments according to the invention, the mentioned cooling crystallization temperature is selected from 20° C. to 30° C.

In some embodiments according to the invention, the ester solvent is selected from the group consisting of ethyl acetate, isopropyl acetate and propyl acetate.

In some embodiments according to the invention, the ester solvent is ethyl acetate.

In some embodiments according to the invention, the alcoholic solvent is selected from the group consisting of methanol, ethanol, isopropanol and tertiary butanol.

In some embodiments according to the invention, the mentioned mixed solvent of the alcoholic solvent with water is selected from the group consisting of methanol/water, ethanol/water and isopropanol/water.

In some embodiments according to the invention, the volume ratio of the alcohol to water is selected from 1:0.5 to 1:1.

In some embodiments according to the invention, the volume ratio of the alcohol to water is 1:1.

The invention further provides pharmaceutical composition containing therapeutically effective amount of the crystal form A mentioned above and pharmaceutically acceptable carrier.

The invention further provides the application of the crystal form A mentioned above and the composition thereof in preparing drug for treating disease associated with PDE2 inhibitor and TNF-α inhibitor.

The invention further provides application of the crystal form A mentioned above and composition thereof in preparing drug for treating liver disease.

In some embodiments according to the invention, the mentioned liver disease is selected from fatty hepatitis and liver fibrosis.

The crystal form of the invention shows good stability and is convenient during preparing drugs.

Definitions and Description

Unless otherwise specified, the following terms and phrases used herein are intended to comprise the following meanings. A particular phrase or term should not be considered as uncertain or unclear in the absence of a specific definition, but should be understood as per its ordinary meaning. A commodity name arising herein is intended to refer to corresponding commodity or the active ingredient thereof.

The intermediate compounds in the invention can be prepared through a variety of synthetic methods known to those skilled in the art, including the embodiments listed below, and embodiments formed by combination of the embodiments listed below with other chemical synthetic methods, and equivalent substitutions known to those skilled in the art. The preferred embodiments include but are not limited to the embodiments according to the invention.

The chemical reactions in the embodiments according to the invention are completed in appropriate solvents, which must be applicable to chemical changes and required reagents and materials thereof according to the invention. In order to obtain the compounds according to the invention, sometimes it is necessary for those skilled in the art to modify or select synthetic steps or reaction processes based on the existing embodiments.

An important consideration factor in planning any synthesis route in this field is to select appropriate protecting groups for reactive functional groups, such as the amino group in the invention. For trained practitioners, *Protective Groups in Organic Synthesis* (Wiley and Sons, 1991) of Greene and Wuts is authoritative in this regard. All references cited in the invention are incorporated into the invention.

The invention will be specifically described below in conjunction with examples, which are not intended to limit the invention in any way.

All solvents used in the invention are available on the market, and can be used without further purification. The reactions are generally carried out in an inert nitrogen atmosphere in an anhydrous solvent. The proton nuclear magnetic resonance data are recorded in a Bruker Avance III 400 (400 MHz) spectrometer, and the chemical shift is expressed in (ppm) downfield of tetramethylsilane. The mass spectrum is measured by Agilent 1200 series and 6110 (&1956A). LC/MS or Shimadzu MS includes DAD: SPD-M20A (LC) and Shimadzu Micromass 2020 detector. The mass spectrometer is equipped with an electrospray ionization source (ESI) that operates in a positive or negative mode.

The following abbreviations are used in the invention: DCM represents dichloromethane; PE represents petroleum ether; EA represents ethyl acetate; DMF represents N,N-dimethylformamide; DMAC represents N,N-dimethylacetamide; DMSO represents dimethylsulfoxide; EtOAc represents ethyl acetate; tol represents toluene; THF represents tetrahydrofuran; EtOH represents ethanol; MeOH represents methanol; NMP represents N-methylpyrrolidone; 2-METHF represents 2-methyltetrahydrofuran; i-PrOH represents 2-propanol; Bn represents benzyl; Cbz represents carbobenzoxy, and it is an amine protecting group; Boc represents tertiary butylcarbonyl, and it is an amine protecting group; Fmoc represents fluorenylmethoxycarbonyl, and it is an amine protecting group; Alloc represents allyloxycarbonyl, and it is an amine protecting group; Teoc represents trimethylsilylethoxycarbonyl, and is an amine protecting group; $Boc_2O$ represents di-tert-butyl dicarbonate; HCl (g) represents hydrogen chloride gas; $H_2SO_4$ represents sulfuric acid; HOAc represents acetic acid; TFA represents trifluoroacetic acid; DIPEA represents diisopropylethylamine; DIEA represents diisopropylethylamine; NMM represents N-methylmorpholine; DBU represents 1,8-diazabicycloundec-7-ene; $Et_3N$ represents triethylamine; LDA represents lithium diisopropylamide; NaHMDS represents sodium bis(trimethylsilyl)amide; KHMDS represents potassium bis(trimethylsilyl)amide; $LiAlH_4$ represents lithium aluminum hydride; t-BuOK represents potassium tert-butoxide; $H_2O_2$ represents hydrogen peroxide; $NH_4Cl$ represents ammonium chloride; $BaSO_4$ represents barium sulfate; $CaCO_3$ represents calcium carbonate; $SnCl_2$ represents stannous chloride; $Zn(BH_4)_2$ represents zinc borohydride; $PPh_3$ represents triphenylphosphine; HMDS represents hexamethyldisilazane; Pd/C represents palladium on activated carbon; $PtO_2$ represents platinum dioxide; $Pd(OH)_2$ represents platinum hydroxide; $Pd_2(dba)_3$ represents tris(dibenzylideneacetone)dipalladium; $Pd(PPh_3)_4$ represents tetrakis(triphenylphosphine)palladium; $Pd(dppf)Cl_2$ represents 1,1'-bis[(diphenylphosphino)ferrocene]dichloropalladium; $Pd(PPh_3)_2Cl_2$ represents dichlorobis(triphenylphosphine)platinum (II); $Pd(OAc)_2$ represents palladium acetate; $PdCl_2$ represents palladium chloride; CuI represents iodide copper; CuBr represents cuprous bromide; CuCl represents cuprous chloride; Cu represents copper powder; $Cu_2O$ represents cuprous oxide; Xantphos represents 4,5-bis(diphenylphosphino)-9,9-dimethylxanthene; Sphos represents 2-dicyclohexylphosphino-2',6'-dimethoxybiphenyl; Xphos represents 2-dicyclohexylphosphino-2',4',6'-triisopropyl-biphenyl; Ruphos represents 2-dicyclohexylphosphino-2',6'-diisopropoxy-1,1'-biphenyl; and Brettphos represents 2-(dicyclohexylphosphino)-3,6-dimethoxy-2',4',6'-triisopropyl-1,1'-biphenyl.

The compounds are named artificially or by ChemDraw® software, and the compounds available on the market are named as per suppliers' catalogs.

X-Ray Powder Diffractometer (XRPD) According to the Invention

Instrument: Bruker D8 ADVANCE X-ray diffractometer;
Method: target: Cu: K-Alpha;
Wavelength λ=1.54179 Å;
Tube voltage: 40 kV;
Tube current: 40 mA; scan area: 4-40°;
Sample rotation speed: 15 rpm;
Scanning speed: 10°/min.

Differential Scanning Calorimeter (DSC) According to the Invention

Instrument: TA Q2000 differential scanning calorimeter;
Method: about 1 mg of sample is presented in an aluminum pot of DSC and is tested as follows: RT-300° C., heating rate: 10° C./min.

Thermal Gravimetric Analyzer (TGA) According to the Invention

Instrument: TA Q5000 thermal gravimetric analyzer;
Method: 2-5 mg of sample is presented in a platinum pot of a TGA and is tested as follows: RT-300° C., heating rate: 10° C./min.

DESCRIPTION OF THE EMBODIMENTS

Figure 1:
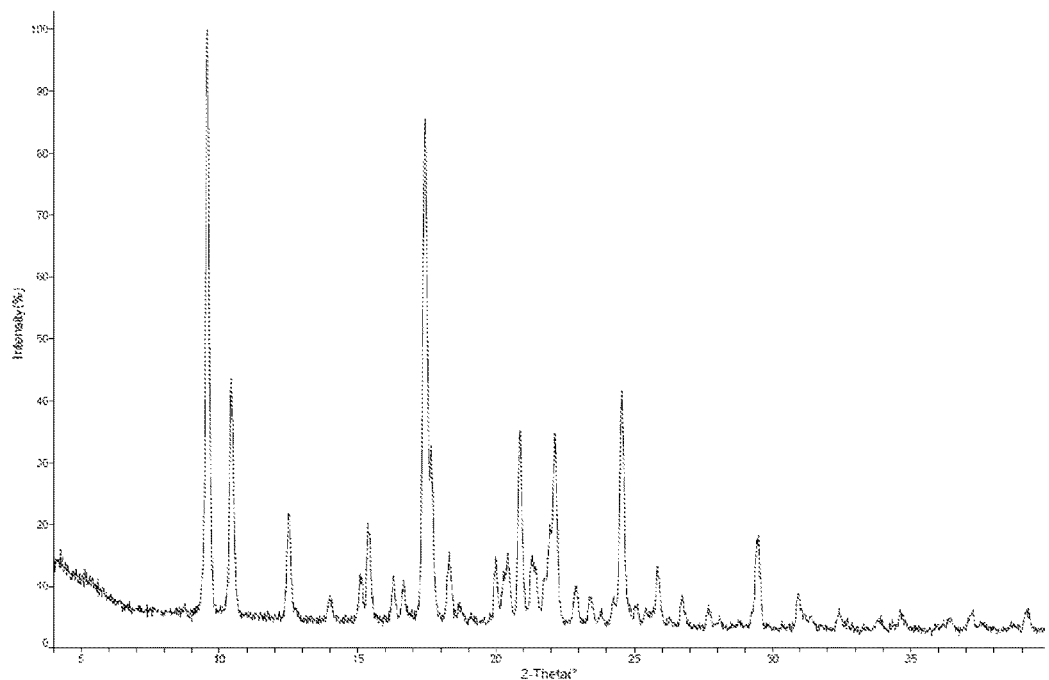
FIG. 1 is an XPRD pattern of crystal form A using Cu-Kα radiation.

In order to make the contents of the invention be more clearly understood, the invention is further described below in conjunction with the embodiments, which, however, are not limitations to the contents of the invention.

Example 1

7-(cyclopropylmethyl)-1-(((cis)-4-hydroxy-4-methylcyclohexyl)methyl)-3-methyl-1H-purine-2,6-(3H,7H)-dione

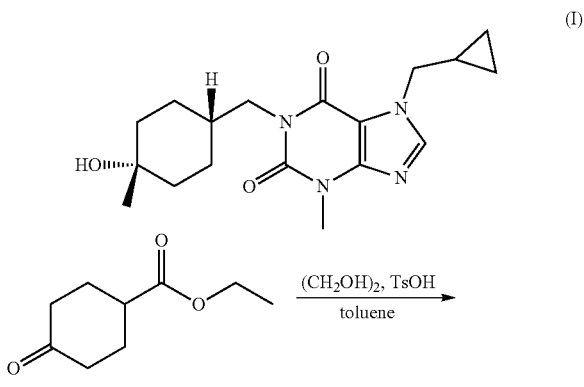

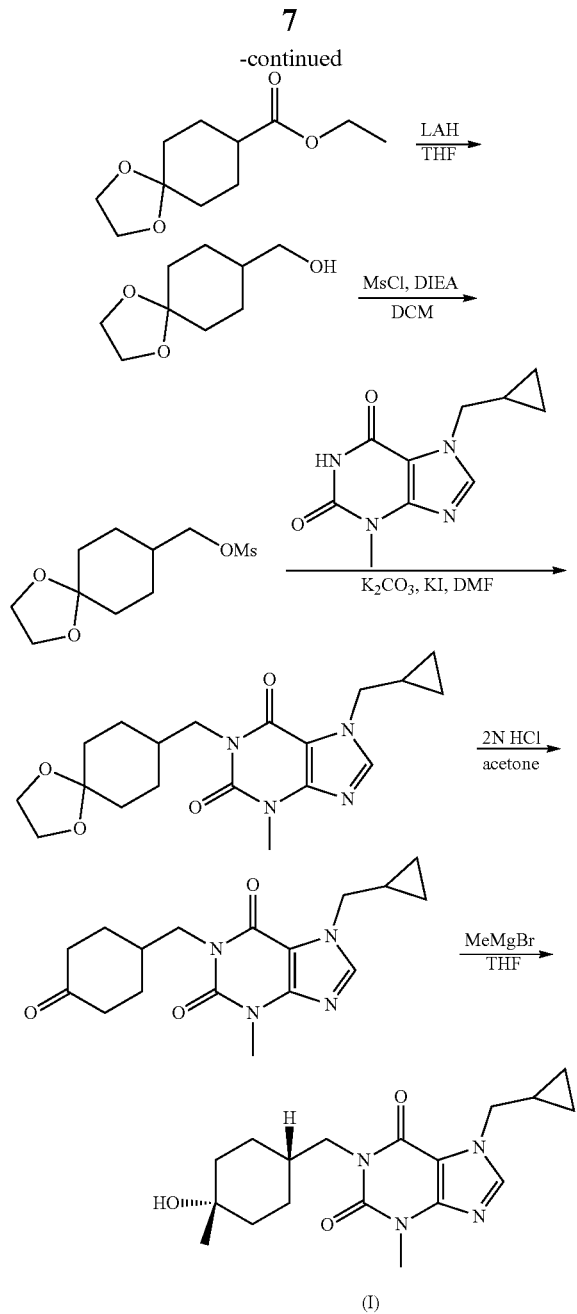

Step 1: ethyl
1,4-dioxaspiro[4,5]decan-8-carboxylate

The solution of ethyl 4-oxocyclohexanedicarboxylate (30.0 g, 176 mmol), ethanediol (22.0 g, 353 mmol) and p-methylbenzenesulfonic acid (304 mg, 1.70 mmol) in methylbenzene (315 mL) was refluxed in Dean-Stark vessel overnight. The reaction solution was cooled to room temperature, and was successively washed with water (300 mL×2) and saturated sodium bicarbonate (500 mL×2). The organic phase was dried with anhydrous magnesium sulfate, and filtered. The filtrate was concentrated under reduced pressure, and the residue was purified by silica gel column chromatography (1:1, petroleum ether/ethyl acetate, Rf=0.3) to obtain the product ethyl 1, 4-dioxaspiro[4,5]decan-8-carboxylate (37.2 g, yellow liquid) with yield of 99%. MS-ESI calculated value: [M+H]+ 215, measured value: 215.

Step 2: 1,4-dioxaspiro[4,5]decan-8-yl-methanol

Lithium aluminum hydride (2.30 g, 61.0 mmol) was slowly added to tetrahydrofuran (60 mL) under nitrogen atmosphere at 0° C., and then a solution of ethyl 1,4-dioxaspiro[4,5]decan-8-carboxylate (10.0 g, 42.0 mmol) in tetrahydrofuran (40 mL) was added dropwise. The resulting solution was slowly heated to 25° C., and was stirred for 3.5 hours. The reaction solution was cooled to 0° C., and then added water (2.30 g, 127 mmol), 15% sodium hydroxide (2.30 g, 8.60 mmol) and water (6.9 g, 383 mmol). The resulting solution was filtered, and the filter cake was washed with tetrahydrofuran (50 mL×3). The organic phase was combined, dried with anhydrous sodium sulfate, and was filtered. The filtrate was concentrated under reduced pressure to obtain the product 1,4-dioxaspiro[4,5]decan-8-yl-methanol (6.22 g, yellow liquid) with yield of 89%. MS-ESI calculated value: [M+H]$^+$ 173, measured value: 173.

Step 3: 1,4-dioxaspiro[4,5]decan-8-yl-methylmethanesulfonate 1,4-dioxaspiro[4,5]decan-8-yl-methanol (2.00 g, 12.0 mmol) and diisopropylethylamine (3.10 g, 24.0 mmol) were dissolved in dichloromethane (40 mL), and methanesulfonyl chloride (3.90 g, 30.0 mmol) was slowly added at 0° C. The reaction solution was heated to 25° C., and stirred overnight. Ammonium chloride saturated aqueous solution (100 mL) was added to quench the reaction, and the resulting solution was extracted with ethyl acetate (200 mL×3). The organic phase was combined, dried with anhydrous magnesium sulfate, and filtered. The filtrate was concentrated under reduced pressure, and separated and purified by silica gel column chromatography (3:1 petroleum ether/ethyl acetate, Rf=0.4) to obtain the product 1,4-dioxaspiro[4,5]decan-8-yl-methylmethanesulfonate (1.80 g, yellow liquid) with yield of 60%. MS-ESI calculated value: [M+H]$^+$ 251, measured value: 251.

Step 4: 1-(1,4-dioxaspiro[4,5]decan-8-yl-methyl-7-(cyclopropylmethyl)-3-methyl-1H-purine-2,6-(3H, 7H)-dione 1,4-dioxaspiro[4,5]decan-8-yl-methylmethanesulfonate (682 mg, 2.72 mmol), 7-(cyclopropylmethyl)-3-methyl-1H-purine-2,6-(3H,7H)-dione (500 mg, 2.27 mmol) and potassium iodide (37.7 mg, 0.227 mmol) were dissolved in N,N-dimethylformamide (10 mL), potassium carbonate (627 mg, 4.54 mmol) was added, and the resulting solution was refluxed while heating at 130° C. for 4 hours. The reaction solution was cooled to room temperature, and was filtered. The filtrate was concentrated under reduced pressure to obtain a crude product 1-(1,4-dioxaspiro[4,5]decan-8-yl-methyl-7-(cyclopropylmethyl)-3-methyl-1H-purine-2, 6-(3H, 7H)-dione (1.10 g, yellow oily). MS-ESI calculated value: [M+H]$^+$ 375, measured value: 375.

Step 5: 7-(cyclopropylmethyl)-3-methyl-1-((4-oxocyclohexyl)methyl)-1H-purine-2,6-(3H,7H)-dione 1-(1,4-dioxaspiro[4,5]decan-8-yl-methyl-7-(cyclopropylmethyl)-3-methyl-1H-purine-2,6-(3H, 7H)-dione (1.20 g, 2.09 mmol) was dissolved in acetone (12 mL), and 4N hydrochloric acid water solution (3 mL) was added. The reaction solution was cooled to room temperature, and was stirred overnight. Water (20 mL) was added, the resulting solution was extracted with ethyl acetate (30 mL×3), the organic phase was dried with anhydrous magnesium sulfate, and the resulting solution was filtered. The filtrate was concentrated under reduced pressure, and the resulting product was purified by silica gel column chromatography (1:1, petroleum ether/ethyl acetate, Rf=0.3) to obtain the product 7-(cyclopropylmethyl)-3-methyl-1-((4-oxocyclohexyl)methyl)-1H-purine-2,6-(3H,7H)-dione (52.0 mg, yellow solid) with yield of 8%. MS-ESI calculated value: $[M+H]^+$ 331, measured value: 331.

Step 6: 7-(cyclopropylmethyl)-1-(((cis)-4-hydroxy-4-methylcyclohexyl)methyl)-3-methyl-1H-purine-2,6-(3H, 7H)-dione 7-(cyclopropylmethyl)-3-methyl-1-((4-oxocyclohexyl)methyl)-1H-purine-2,6-(3H,7H)-dione (100 mg, 0.303 mmol) was dissolved in tetrahydrofuran (5 mL), and a methyl Grignard reagent (3 M ethyl ether solution, 0.60 mL, 1.8 mmol) was slowly added under nitrogen protection at −78° C. The resulting solution was stirred at −78° C. for half an hour, and then kept at 0° C. for 2 hours. Water (10 mL) was slowly added dropwise to quench the reaction, and the reaction solution was extracted with ethyl acetate (30 mL×3). The organic phase was combined, dried with anhydrous magnesium sulfate, and was filtered. The filtrate was concentrated under reduced pressure to obtain a crude product, which was purified by high performance liquid chromatography to obtain the product 7-(cyclopropylmethyl)-1-(((cis)-4-hydroxy-4-methylcyclohexyl)methyl)-3-methyl-1H-purine-2,6-(3H, 7H)-dione (42.0 mg, white solid) as compound (I), with yield of 40%. $^1$H NMR: (400 MHz, methonal-$d_4$) δ7.99 (s, 1H), 4.19 (d, J=8.0 Hz, 2H), 3.89 (d, J=8.0 Hz, 2H), 3.54 (s, 3H), 1.81-1.70 (m, 1H), 1.69-1.62 (m, 2H), 1.51-1.41 (m, 4H), 1.39-1.25 (m, 3H), 1.15 (s, 3H), 0.63-0.56 (m, 2H), 0.48-0.42 (m, 2H).

MS-ESI calculated value: $[M+H-H_2O]^+$ 329, measured value: 329.

Step 7: Preparation of Crystal Form A 7-(cyclopropylmethyl)-1-(((cis)-4-hydroxy-4-methylcyclohexyl)methyl)-3-methyl-1H-purine-2,6-(3H, 7H)-dione (42.0 mg) was dissolved in ethyl acetate (10 mL) while heating at 50° C. The solution was concentrated under reduced pressure to 0.5 mL to separate out a solid, and the mixture was stirred at room temperature overnight. The mixture was filtered, and the filter cake was collected. The filter cake was dried under vacuum to obtain the crystal form A.

Experimental Example 1: In Vitro Evaluation on Inhibition Activities of PDE2 Phosphodiesterase Experimental objective: the concentrations of AMP/GMP generated in the reaction system was detected by detecting a substituted AlexaFluor 633 fluorochrome on AMP/GMP antibodies through fluorescence polarization analysis, and $IC_{50}$ of PDE2 phosphodiesterase against compound to be detected was calculated.

Experimental Materials:
Buffer solution for determination: 10 mM Tris-HCl, pH 7.5, 5 mM $MgCl_2$, 0.01% Brij 35, 1 mM DTT, and 1% DMSO.

Enzyme: A recombinant full-length human PDE2A protein was expressed by baculovirus in Sf9 insect cells using an N-terminal GST tag
Substrate: 1 μM cGMP
Test Method:
Transcreener® $AMP^2/GMP^2$ antibody, AMP2/GMP2 AlexaFluor 633 fluorochrome
Experimental Operations:

An enzyme solution was prepared from a freshly prepared buffer solution, and then added to a reaction cavity, a DMSO solution of compound to-be-detected was added through an Echo550 contactless nanoliter pipetting system, and then the resulting solution was preincubated for 10 min at room temperature. A substrate (1 μM cGMP) was added to initiate reaction, which was kept at room temperature for 1 h. Then a detection system (Transcreener® $AMP^2/GMP^2$ antibodies, AMP2/GMP2 AlexaFluor 633 fluorochromes) was added, and kept at room temperature for 90 min. Fluorescence polarization was detected using Ex/Em 620/688.

Fluorescence polarization intensity was converted to nM concentration through AMP/GMP standard curves, then relative enzymatic activity inhibition was calculated compared with DMSO blank control, and $IC_{50}$ and curve thereof was calculated using Prism software package (GraphPad Software, San Diego Calif., USA).

Experimental Results:

TABLE 2

Test Results of Inhibition Activities of PDE2 Phosphodiesterase

| Test Sample | Inhibition Activities of PDE2 Phosphodiesterase |
|---|---|
| Compound (I) | ++ |

Note:
1 μM ≤ "++" < 10 μM.

Conclusion: the compound (I) showed significant or even unexpected PDE2A protease inhibition activities.

Experimental Example 2: In Vitro Evaluation on Influence of Compound on LPS-Induced TNF-α in Blood of Mice Experimental objective: to detect the influence of compound on LPS-induced TNF-α in blood of mice in vitro, and to evaluate inhibiting effects of the compound on LPS-induced TNF-α in blood of mice.

Experimental Materials:
Sprague Dawley rats (male, 210-260 g, 8-10 weeks old, Shanghai SLAC)
Rat TNF-alpha Quantikine ELISA Kit (R&D, #SRTA00)
Experimental Operations:

The solution of compound to-be-detected at a concentration of 1 mM was prepared, and 40 μL (final concentration of the compound: 100 uM) was respectively added to a 48-well cell culture plate. After rats were anesthetized with isoflurane, blood samples were collected from their hearts (heparin anticoagulation). The blood was added to the to-be-detected compound present in the 48-well plate with 320 μL/well. The 48-well plate was incubated in a cell incubator for 30 min. Then 40 μL of LPS solution (100 ug/ml) was added, and fully mixed. The plate was further incubated in the incubator. 5 h later, the 48-well plate was taken out. The blood samples were transferred to 1.5 ml centrifuge tubes, and centrifuged in a centrifuge (4,500 rpm, 4° C., 5 minutes). The supernatant was separated to obtain blood plasma, which was subpackaged, quickly frozen, and kept in a refrigerator at −80° C. On the next day, the TNF-α levels in blood plasma samples were detected using an R&D ELISA kit.

Experimental Results:

TABLE 3

Test Results of TNF-α Inhibition Activities

| Test Sample | TNF-α Inhibition Ratio |
|---|---|
| Chemical compound (I) | ++ |

Note:
80% ≤ "++" < 100%.

Conclusion: the compound according to the invention showed significant or even unexpected TNF-α inhibition activities.

Experimental Example 3: Evaluation on Pharmacokinetics of Compound

Experimental objective: To test the pharmacokinetics of a compound in SD rats

Experimental materials: Sprague Dawley rats (male, 200-300 g, 7-9 weeks old, Shanghai SLAC)

Experimental Operations:

Pharmacokinetic characteristics of rodents after intravenous injection and oral administration of the compound were tested using a standard scheme. In the experiment, a candidate compound was prepared into a clear solution, which was administrated to rats by single intravenous injection and oral administration. The solvent for intravenous injection and oral administration is water solution or normal saline solution of hydroxypropyl β cyclodextrin at a certain proportion. A whole blood sample was collected within 24 hours, and 3000 g of the sample was centrifuged for 15 minutes. The supernatant was separated to obtain blood plasma samples, to which 4 times volume of an acetonitrile solution containing an internal standard substance was added to precipitate protein. After centrifuging, the supernatant was collected, equivalent volume of water was added, the resulting solution was recentrifuged, and the supernatant was collected for sample injection. The blood concentration was quantitatively analyzed by LC-MS/MS, and the pharmacokinetic parameters were calculated, such as peak concentration, time to peak, clearance rate, half life, area under the curve and bioavailability.

Experimental Results:

TABLE 4

Pharmacokinetic Test Results

| Test Sample | Clearance rate (mL/min/kg) | Half life $T_{1/2}$ (h) | Concentration integral AUC (nM · hr) | Bioavailability F (%) |
|---|---|---|---|---|
| Pentoxifylline | 74.1 | 0.191 | 6622 | |
| Compound (I) | 54.4 | 0.793 | 4390 | 47.9 |

Conclusion: the compound (I) can significantly improve an individual or some pharmacokinetic indexes of rats.

Experimental Example 4: Solubility of Crystal Form A in Different Solvents

About 2 mg of crystal form A was weighed put in a 1.5 mL liquid phase vial, to which the following solvents were respectively added by pipettes by stages to dissolve the crystal form A while manually vibrating. The test was performed at room temperature, and the dissolution was determined by naked eyes, as shown in Table 5.

TABLE 5

Solubility of Crystal Form A in Different Solvents

| No. | Solvent | Solubility (mg/mL) |
|---|---|---|
| 1 | Methanol | ~28.7 |
| 2 | Ethanol | ~11.2 |
| 3 | Isopropanol | ~10.1 |
| 4 | n-butanol | ~20.5 |
| 5 | Acetonitrile | ~13.0 |
| 6 | Acetone | ~17.2 |
| 7 | Butanone | ~37.2 |
| 8 | Methyl isobutyl ketone | ~10.9 |
| 9 | Ethyl acetate | ~15.2 |
| 10 | Isopropyl acetate | ~12.0 |
| 11 | Methyl tertiary butyl ether | ~2.6 |
| 12 | Tetrahydrofuran | >67.0 |
| 13 | 2-methyltetrahydrofuran | ~24.2 |
| 14 | Methylbenzene | <1.0 |
| 15 | n-heptane | <1.0 |
| 16 | Cyclohexane | <1.0 |
| 17 | Dioxane | >57.0 |
| 18 | Water | <1.0 |
| 19 | Methanol-water (1:1) | ~7.8 |
| 20 | Methanol-water (3:1) | ~19.0 |
| 21 | Ethanol-water (1:1) | ~16.3 |
| 22 | Ethanol-water (3:1) | ~24.5 |
| 23 | Acetonitrile-water (1:1) | ~22.2 |
| 24 | Acetone-water (1:2) | ~1.0 |
| 25 | Isopropanol-water (1:1) | ~17.3 |

Experimental Example 5: Stability Test of Crystal Form a Solid

A crystal form A was put in an open container at a constant temperature and humidity for accelerated test respectively at 40° C./75% humidity (open). Samples were collected in 1st, 2nd and 3rd months and tested, and the test results were compared with the initial test results on 0th day. The test results are shown in Table 6 below:

TABLE 6

Stability Test of Crystal Form A Solid

| Test conditions | Sampling time (month) | Appearance | Content (%) | Total Impurities (%) |
|---|---|---|---|---|
| Initial | 0 | White powder | 101.6 | 0.33 |
| 40° C./75% humidity (open) | 1 | White powder | 101.4 | 0.31 |
| 40° C./75% humidity (open) | 2 | White powder | 98.8 | 0.34 |
| 40° C./75% humidity (open) | 3 | White powder | 101.8 | 0.32 |

The invention claimed is:

1. A crystal form A of 7-(cyclopropylmethyl)-1-(((cis)-4-hydroxy-4-methylcyclohexyl)methyl)-3-methyl-1H-purine-2,6-(3H,7H)-dione of formula (I):

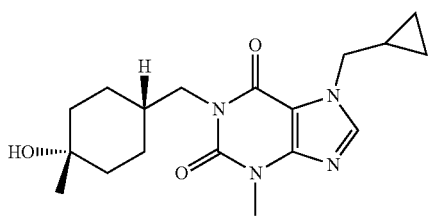

wherein the crystal form A is characterized by an X-ray powder diffraction pattern comprising peaks (2θ) at 9.578°, 10.430°, 12.502°, 15.380°, 17.428°, 17.646°, 20.879°, 22.141°, 24.548° and 29.477°.

2. The crystal form A according to claim 1, wherein the crystal form A is characterized by an X-ray powder diffraction pattern further comprising peaks (2θ) at 13.996°, 15.086°, 16.287°, 16.661°, 18.298°, 19.977°, 20.427°, 21.314°, 22.928°, 23.387°, 24.270°, 25.116°, 25.834°, 26.719°, 27.665°, 30.956°, 32.416°, 34.623°, 37.243° and 39.237°.

3. The crystal form A according to claim 1, wherein the crystal form A is characterized by an X-ray powder diffraction pattern as shown in FIG. 1.

Figure 2:
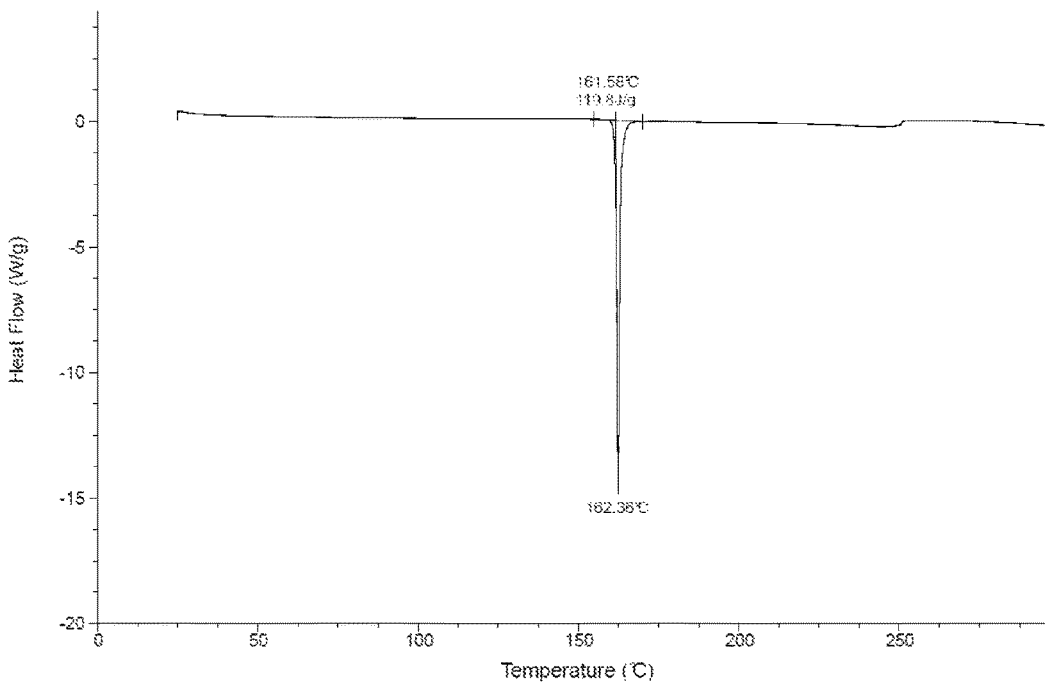
FIG. 2 is a DSC diagram of crystal form A.

4. The crystal form A according to claim 1, wherein the crystal form A is characterized by a differential scanning calorimetry thermogram as shown in FIG. 2.

Figure 3:
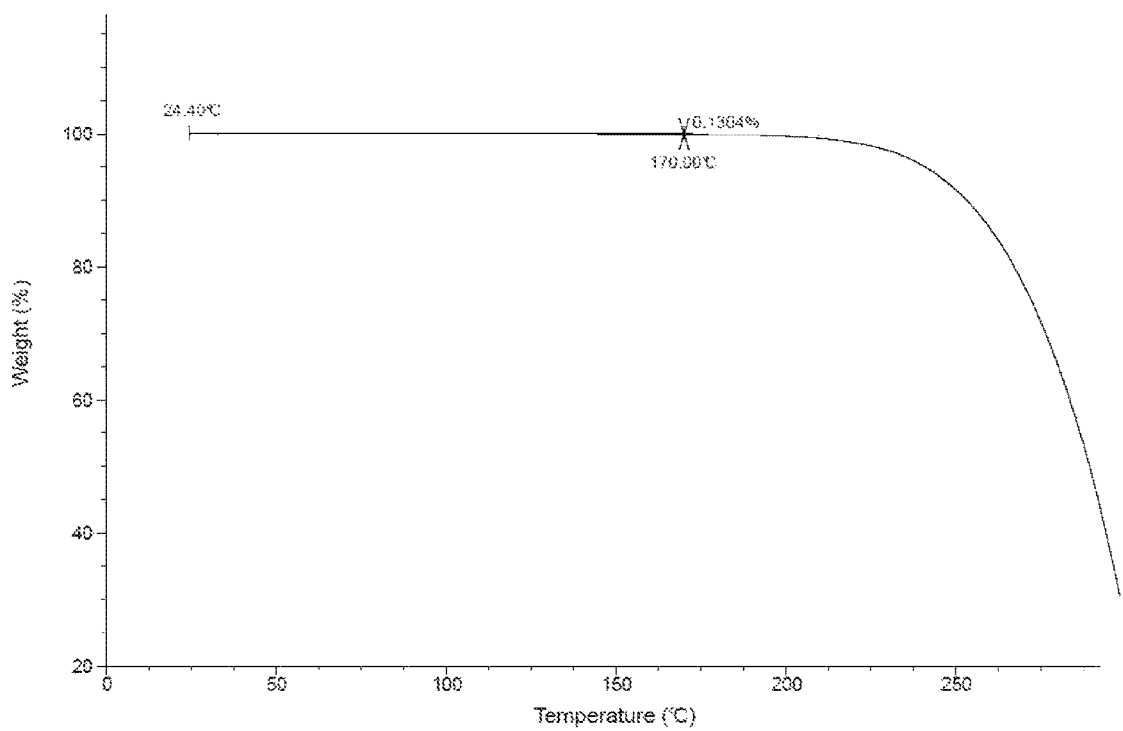
FIG. 3 is a TGA diagram of crystal form A.

5. The crystal form A according to claim 1, wherein the crystal form A is characterized by a thermogravimetric analysis curve as shown in FIG. 3.

6. A pharmaceutical composition comprising a therapeutically effective amount of the crystal form A according to claim 1 and a pharmaceutically acceptable carrier.

7. A method for inhibiting phosphodiesterase 2 activity in a mammal, comprising administering to the mammal a therapeutically effective amount of the crystal form A according to claim 1.

8. The method according to claim 7, wherein the mammal has a liver disease.

9. The method according to claim 8, wherein the liver disease is selected from the group consisting of fatty hepatitis and liver fibrosis.

10. A method for inhibiting tumor necrosis factor-alpha activity in a mammal, comprising administering to the mammal a therapeutically effective amount of the crystal form A according to claim 1.

11. The method according to claim 10, wherein the mammal has a liver disease.

12. The method according to claim 11, wherein the liver disease is selected from the group consisting of fatty hepatitis and liver fibrosis.

13. A process for preparing the crystal form A according to claim 1, wherein the process comprises the following steps:
(1) dissolving 7-(cyclopropylmethyl)-1-(((cis)-4-hydroxy-4-methylcyclohexyl)methyl)-3-methyl-1H-purine-2,6-(3H,7H)-dione in ethyl acetate at a temperature in the range of 20° C. to 77.1° C. (room temperature to reflux);
(2) cooling the solution to room temperature; and
(3) isolating the crystal form A according to claim 1.

14. The process according to claim 13, wherein the process further comprises removing 1/30 to 1/2 of the total amount of ethyl acetate under reduced pressure prior to step (2).

15. The process according to claim 13, wherein the ratio of the mass of 7-(cyclopropylmethyl)-1-(((cis)-4-hydroxy-4-methylcyclohexyl)methyl)-3-methyl-1H-purine-2,6-(3H, 7H)-dione to the mass of ethyl acetate ranges from 1:10 to 1:250.

16. The process according to claim 13, wherein step (1) further comprises dissolving 7-(cyclopropylmethyl)-1-(((cis)-4-hydroxy-4-methylcyclohexyl)methyl)-3-methyl-1H-purine-2,6-(3H,7H)-dione in ethyl acetate at a temperature in the range of 40° C. to 60° C.

17. The process according to claim 13, wherein step (3) further comprises crystallizing the crystal form A of 7-(cyclopropylmethyl)-1-(((cis)-4-hydroxy-4-methylcyclohexyl)methyl)-3-methyl-1H-purine-2,6-(3H,7H)-dione from ethyl acetate at a temperature in the range of 0° C. to 30° C.

* * * * *